US009308009B2

(12) United States Patent  (10) Patent No.: US 9,308,009 B2
Madan et al.  (45) Date of Patent: Apr. 12, 2016

(54) SURGICAL INSTRUMENT WITH MODULAR SHAFT AND TRANSDUCER

(75) Inventors: Ashvani K. Madan, Mason, OH (US); John V. Hunt, Cincinnati, OH (US); Kevin L. Houser, Springboro, OH (US)

(73) Assignee: Ethicon Endo-Surgery, LLC, Los Frailes Industrial Park Guaynabo, PR (US)

( * ) Notice: Subject to any disclaimer, the term of this patent is extended or adjusted under 35 U.S.C. 154(b) by 934 days.

(21) Appl. No.: 13/270,684

(22) Filed: Oct. 11, 2011

(65) Prior Publication Data

US 2012/0116395 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 18/14*  (2006.01)
*A61B 17/28*  (2006.01)
(Continued)

(52) U.S. Cl.
CPC ....... *A61B 17/2812* (2013.01); *A61B 17/00234* (2013.01); *A61B 17/320068* (2013.01); *A61B 17/320092* (2013.01); *A61B 18/00* (2013.01); *A61B 18/04* (2013.01); *A61B 18/12* (2013.01); *A61B 18/14* (2013.01); *A61B 18/1442* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 19/38* (2013.01); *A61B 19/56* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); 
(Continued)

(58) Field of Classification Search
USPC ........................................... 606/21, 169–170
See application file for complete search history.

(56) References Cited

U.S. PATENT DOCUMENTS 1,754,806 A    4/1930   Stevenson
3,297,192 A    1/1967   Swett
(Continued)

FOREIGN PATENT DOCUMENTS

DE    102008051866    10/2010
DE    102009013034    10/2010
(Continued)

OTHER PUBLICATIONS

U.S. Appl. No. 13/151,471, Jun. 2, 2011, Stulen.
(Continued)

*Primary Examiner* — Paula J Stice (57) ABSTRACT

An ultrasonic surgical device comprises a detachable transducer module, a handle, and a shaft assembly. The shaft assembly includes an end effector having a harmonic blade. The transducer module is removably coupled with the shaft assembly to form an active assembly. The active assembly is removably coupled with the handle. The handle may include a resilient wall structure that deflects outwardly to receive the active assembly in a snap fit. The handle may include a pivoting latch feature to selectively retain the active assembly relative to the handle.

18 Claims, 6 Drawing Sheets

(51) Int. Cl.
*A61B 17/00* (2006.01)
*A61B 17/32* (2006.01)
*A61B 18/00* (2006.01)
*A61B 18/04* (2006.01)
*H02J 7/00* (2006.01)
*H01M 2/26* (2006.01)
*H01M 2/10* (2006.01)
*A61B 18/12* (2006.01)
*A61B 19/00* (2006.01)
*A61B 17/064* (2006.01)
*A61B 17/285* (2006.01)
*A61B 17/29* (2006.01)

(52) U.S. Cl.
CPC ..... *A61B2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekumas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,871,493 A | 2/1999 | Sjostrom et al. |
| 5,873,873 A | 2/1999 | Smith et al. |
| 5,882,310 A | 3/1999 | Marian, Jr. |
| 5,893,835 A | 4/1999 | Witt et al. |
| 5,893,874 A | 4/1999 | Bourque et al. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francischelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |

(56) References Cited

U.S. PATENT DOCUMENTS

| | | |
|---|---|---|
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,551,088 B2 | 10/2013 | Falkenstein et al. |
| 8,564,242 B2 | 10/2013 | Hansford et al. |
| 8,573,461 B2 | 11/2013 | Shelton, et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 9,044,261 B2 | 6/2015 | Houser |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0105750 A1 | 4/2009 | Price et al. |
| 2009/0125026 A1 | 5/2009 | Rioux et al. |

(56) References Cited

U.S. PATENT DOCUMENTS

| | | | |
|---|---|---|---|
| 2009/0137952 A1 | 5/2009 | Ramamurthy et al. | |
| 2009/0138006 A1 | 5/2009 | Bales et al. | |
| 2009/0143797 A1 | 6/2009 | Smith et al. | |
| 2009/0143798 A1 | 6/2009 | Smith et al. | |
| 2009/0143799 A1* | 6/2009 | Smith et al. | 606/169 |
| 2009/0143800 A1 | 6/2009 | Deville et al. | |
| 2009/0143801 A1 | 6/2009 | Deville et al. | |
| 2009/0143802 A1 | 6/2009 | Deville et al. | |
| 2009/0143803 A1 | 6/2009 | Palmer et al. | |
| 2009/0143804 A1 | 6/2009 | Palmer et al. | |
| 2009/0143805 A1 | 6/2009 | Palmer et al. | |
| 2009/0209979 A1 | 8/2009 | Yates et al. | |
| 2009/0209990 A1 | 8/2009 | Yates et al. | |
| 2009/0240246 A1 | 9/2009 | Deville et al. | |
| 2009/0253030 A1 | 10/2009 | Kooij | |
| 2009/0264940 A1 | 10/2009 | Beale et al. | |
| 2009/0275940 A1 | 11/2009 | Malackowski et al. | |
| 2009/0281430 A1 | 11/2009 | Wilder | |
| 2009/0281464 A1 | 11/2009 | Cioanta et al. | |
| 2010/0016855 A1 | 1/2010 | Ramstein et al. | |
| 2010/0021022 A1 | 1/2010 | Pittel et al. | |
| 2010/0030218 A1 | 2/2010 | Prevost | |
| 2010/0060231 A1 | 3/2010 | Trainor et al. | |
| 2010/0069940 A1* | 3/2010 | Miller et al. | 606/169 |
| 2010/0076455 A1 | 3/2010 | Birkenbach et al. | |
| 2010/0089970 A1 | 4/2010 | Smith et al. | |
| 2010/0106144 A1 | 4/2010 | Matsumura et al. | |
| 2010/0106146 A1 | 4/2010 | Boitor et al. | |
| 2010/0125172 A1 | 5/2010 | Jayaraj | |
| 2010/0152610 A1* | 6/2010 | Parihar et al. | 600/566 |
| 2010/0201311 A1 | 8/2010 | Alexander et al. | |
| 2010/0211053 A1 | 8/2010 | Ross et al. | |
| 2010/0249665 A1 | 9/2010 | Roche | |
| 2010/0268221 A1 | 10/2010 | Beller et al. | |
| 2010/0274160 A1 | 10/2010 | Yachi et al. | |
| 2010/0301095 A1 | 12/2010 | Shelton, IV et al. | |
| 2011/0009694 A1 | 1/2011 | Schultz et al. | |
| 2011/0015660 A1 | 1/2011 | Wiener et al. | |
| 2011/0058982 A1 | 3/2011 | Kaneko | |
| 2011/0074336 A1 | 3/2011 | Miller | |
| 2011/0077514 A1 | 3/2011 | Ulric et al. | |
| 2011/0080134 A1 | 4/2011 | Miller | |
| 2011/0087212 A1 | 4/2011 | Aldridge et al. | |
| 2011/0087218 A1 | 4/2011 | Boudreaux et al. | |
| 2011/0152901 A1 | 6/2011 | Woodruff et al. | |
| 2011/0221398 A1 | 9/2011 | Ferber | |
| 2011/0224668 A1 | 9/2011 | Johnson et al. | |
| 2011/0247952 A1 | 10/2011 | Hebach et al. | |
| 2011/0288573 A1 | 11/2011 | Yates et al. | |
| 2012/0179036 A1 | 7/2012 | Patrick et al. | |
| 2012/0265230 A1 | 10/2012 | Yates et al. | |
| 2012/0283732 A1 | 11/2012 | Lam | |
| 2012/0292367 A1 | 11/2012 | Morgan et al. | |
| 2013/0085330 A1 | 4/2013 | Ramamurthy et al. | |
| 2013/0085332 A1 | 4/2013 | Ramamurthy et al. | |
| 2013/0085397 A1 | 4/2013 | Ramamurthy et al. | |
| 2013/0090528 A1 | 4/2013 | Ramamurthy et al. | |
| 2013/0090530 A1 | 4/2013 | Ramamurthy et al. | |
| 2013/0090552 A1 | 4/2013 | Ramamurthy et al. | |
| 2013/0116690 A1 | 5/2013 | Unger et al. | |
| 2013/0118733 A1 | 5/2013 | Kumar | |
| 2013/0342962 A1 | 12/2013 | Fletcher et al. | |
| 2014/0088739 A1 | 3/2014 | Ellis et al. | |

FOREIGN PATENT DOCUMENTS

| | | | |
|---|---|---|---|
| EP | 0897696 A1 | 2/1999 | |
| EP | 0947167 A1 | 10/1999 | |
| EP | 1330991 A1 | 7/2003 | |
| EP | 152583 A2 | 4/2005 | |
| EP | 1535585 A2 | 6/2005 | |
| EP | 1684396 A2 | 7/2006 | |
| EP | 1721576 A1 | 11/2006 | |
| EP | 1743592 A1 | 1/2007 | |
| EP | 1818021 A1 | 8/2007 | |
| EP | 1839599 | 10/2007 | |
| EP | 1868275 A2 | 12/2007 | |
| EP | 1886637 A1 | 2/2008 | |
| EP | 1943976 A2 | 7/2008 | |
| EP | 1970014 | 9/2008 | |
| EP | 1997439 A2 | 12/2008 | |
| EP | 2027819 A1 | 2/2009 | |
| EP | 2090256 A2 | 8/2009 | |
| EP | 2105104 A2 | 9/2009 | |
| EP | 2165660 A2 | 3/2010 | |
| EP | 2218409 A1 | 8/2010 | |
| EP | 2243439 A1 | 10/2010 | |
| EP | 2345454 A1 | 7/2011 | |
| GB | 2425874 | 11/2006 | |
| GB | 2440566 A | 2/2008 | |
| JP | 4602681 | 12/2010 | |
| JP | 4836148 | 12/2011 | |
| WO | WO 97/24072 | 7/1997 | |
| WO | WO 00/65682 | 2/2000 | |
| WO | WO 03/013374 | 2/2003 | |
| WO | WO 03/020139 | 3/2003 | |
| WO | WO 2004/113991 | 12/2004 | |
| WO | WO 2005/079915 | 9/2005 | |
| WO | WO 2006/023266 | 3/2006 | |
| WO | WO 2007/004515 | 1/2007 | |
| WO | WO 2007/024983 | 3/2007 | |
| WO | WO 2007/090025 | 8/2007 | |
| WO | WO 2007/137115 | 11/2007 | |
| WO | WO 2007/137304 | 11/2007 | |
| WO | WO 2008/071898 | 6/2008 | |
| WO | WO 2008/102154 | 8/2008 | |
| WO | WO 2008/107902 | 9/2008 | |
| WO | WO 2008/131357 | 10/2008 | |
| WO | WO 2009/018409 | 2/2009 | |
| WO | WO 2009/046394 | 4/2009 | |
| WO | WO 2009/070780 | 6/2009 | |
| WO | WO 2009/073608 | 6/2009 | |
| WO | WO 2010/030850 | 3/2010 | |
| WO | WO 2010/096174 | 8/2010 | |
| WO | WO 2011/059785 | 5/2011 | |
| WO | WO 2011/089270 | 7/2011 | |

OTHER PUBLICATIONS

U.S. Appl. No. 13/151,481, Jun. 2, 2011, Yates et al.
U.S. Appl. No. 13/151,488, Jun. 2, 2011, Shelton IV et al.
U.S. Appl. No. 13/151,498, Jun. 2, 2011, Felder et al.
U.S. Appl. No. 13/151,503, Jun. 2, 2011, Madan et al.
U.S. Appl. No. 13/151,509, Jun. 2, 2011, Smith et al.
U.S. Appl. No. 13/151,512, Jun. 2, 2011, Houser et al.
U.S. Appl. No. 13/151,515, Jun. 2, 2011, Felder et al.
U.S. Appl. No. 13/176,875, Jul. 6, 2011, Smith et al.
U.S. Appl. No. 13/269,870, Oct. 10, 2011, Houser et al.
U.S. Appl. No. 13/269,883, Oct. 10, 2011, Mumaw et al.
U.S. Appl. No. 13/269,899, Oct. 10, 2011, Boudreaux et al.
U.S. Appl. No. 13/270,667, Oct. 11, 2011, Timm et al.
U.S. Appl. No. 13/270,684, Oct. 11, 2011, Madan et al.
U.S. Appl. No. 13/270,701, Oct. 11, 2011, Johnson et al.
U.S. Appl. No. 13/271,352, Oct. 12, 2011, Houser et al.
U.S. Appl. No. 13/271,364, Oct. 12, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic BatterySystem," Stryker (2006) pp. 1-2.
U.S. Appl. No. 13/274,480, Oct. 17, 2011, Mumaw et al.
U.S. Appl. No. 13/274,496, Oct. 17, 2011, Houser et al.
U.S. Appl. No. 13/274,507, Oct. 17, 2011, Houser et al.
U.S. Appl. No. 13/274,516, Oct. 17, 2011, Haberstich et al.
U.S. Appl. No. 13/274,540, Oct. 17, 2011, Madan.
U.S. Appl. No. 13/274,805, Oct. 17, 2011, Price et al.
U.S. Appl. No. 13/274,830, Oct. 17, 2011, Houser et al.
U.S. Appl. No. 13/275,495, Oct. 18, 2011, Houser et al.
U.S. Appl. No. 13/275,514, Oct. 18, 2011, Houser et al.
U.S. Appl. No. 13/275,547, Oct. 18, 2011, Houser et al.
U.S. Appl. No. 13/275,563, Oct. 18, 2011, Houser et al.

(56) References Cited

OTHER PUBLICATIONS

U.S. Appl. No. 13/276,660, Oct. 19, 2011, Houser et al.
U.S. Appl. No. 13/276,673, Oct. 19, 2011, Kimball et al.
U.S. Appl. No. 13/276,687, Oct. 19, 2011, Price et al.
U.S. Appl. No. 13/276,707, Oct. 19, 2011, Houser et al.
U.S. Appl. No. 13/276,725, Oct. 19, 2011, Houser et al.
U.S. Appl. No. 13/276,745, Oct. 19, 2011, Stulen et al.
U.S. Appl. No. 13/277,328, Oct. 20, 2011, Houser et al.
International Search Report and Written Opinion dated Jan. 26, 2012for Application No. PCT/US2011/059212.
International Search Report and Written Opinion dated Feb. 2, 2012for Application No. PCT/US2011/059378.
International Search Report dated Feb. 2, 2012for Application No. PCT/US2011/059354.
International Search Report dated Feb. 7, 2012 for Application No. PCT/US2011/059351.
International Search Report dated Feb. 13, 2012for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012for Application No. PCT/US2011/059362.
International Search Report dated Apr. 4, 2012 for Application No. PCT/US2011/059215.
International Search Report dated Apr. 11, 2012 for Application. No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012for Application. No. PCT/US2011/059362.
Communication from International Searching Authority dated Feb. 2, 2012for Application.No. PCT/US2011/059222.
Communication from International Searching Authority dated Jan. 24, 2012 for Application No. PCT/US2011/059215.
Communication from International Searching Authority dated Feb. 2, 2012for Application. No. PCT/US2011/059378.
Machine Translation of the Abstract of German Application No. DE 102009013034.
Machine Translation of German Application No. DE 102008051866.
International Search Report and Written Opinion dated Jul. 6, 2012 for PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.

(56) References Cited

OTHER PUBLICATIONS

Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jan. 5, 2015 for U.S. Appl. No. 13/269,870.
US Office Action, Non-Final, dated Jul. 29, 2014 for U.S. Appl. No. 13/270,667.
US Office Action, Notice of Allowance, dated Dec. 17, 2014 for U.S. Appl. No. 13/270,667.
US Office Action, Restriction Requirement, dated Sep. 11, 2014 for U.S. Appl. No. 13/270,701.
US Office Action, Non-Final, dated Dec. 16, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Notice of Allowance, dated Nov. 28, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/726,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.

(56) References Cited

OTHER PUBLICATIONS

US Office Action, Notice of Allowance, dated Oct. 7, 2014 for U.S. Appl. No. 13/276,745.
US Office Action, Notice of Allowance, dated Dec. 19, 2014 for U.S. Appl. No. 13/276,745.
US Office Action, Restriction Requirement, dated Sep. 24, 2014 for U.S. Appl. No. 13/277,328.
US Office Action, Non-Final, dated Dec. 8, 2014 for U.S. Appl. No. 13/277,328.
Australian First Examination Report dated Jun. 11, 2015 for Application No. AU2011323281.
Chinese First Office Action dated Apr. 16, 2015 for Application No. CN201180063919X.
Chinese First Office Action dated Jun. 1, 2015 for Application NO. CN2011800640981.
US Office Action, Final, dated Apr. 1, 2015, for U.S. Appl. No. 13/151,481.
US Office Action, Notice of Allowance, dated Feb. 25, 2015 for U.S. Appl. No. 13/151,509.
US Office Action, Notice of Allowance, dated Feb. 17, 2015 for U.S. Appl. No. 13/151,512.
US Office Action, Final, dated Aug. 14, 2015 for U.S. Appl. No. 13/269,870.
US Office Action, Non-Final, dated Mar. 26, 2015 for U.S. Appl. No. 13/271,352.
US Office Action, Final, dated Jul. 15, 2015 for U.S. Appl. No. 13/271,352.
US Office Action, Non-Final, dated Jul. 14, 2015 for U.S. Appl. No. 13/271,364.
US Office Action, Non-Final, dated Apr. 2, 2015 for U.S. Appl. No. 13/274,496.
US Office Action, Non-Final, dated Jul. 22, 2015, for U.S. Appl. No. 13/274,507.
US Office Action, Final, dated May 8, 2015 for U.S. Appl. No. 13/274,516.
US Office Action, Notice of Allowance, dated Sep. 28, 2015 for U.S. Appl. No. 13/274,516.
US Office Action, Notice of Allowance, dated Jan. 21, 2015 for U.S. Appl. No. 13/274,540.
US Office Action, Notice of Allowance, dated Jan. 21, 2015 for U.S. Appl. No. 13/274,805.
US Office Action, Notice of Allowance, dated Mar. 23, 2015 for U.S. Appl. No. 13/274,830.
US Office Action, Non-Final, dated Feb. 25, 2015 for U.S. Appl. No. 13/275,495
US Office Action, Final, dated Mar. 10, 2015 for U.S. Appl. No. 13/275,547.
US Office Action, Final, dated Mar. 13, 2015 for U.S. Appl. No. 13/276,673.
US Office Action, Notice of Allowance, dated Dec. 23, 2014 for U.S. Appl. No. 13/276,687.
US Office Action, Non-Final, dated Jan. 29, 2015 for U.S. Appl. No. 13/276,707.
Japanese Notification of Reasons for Refusal dated Aug. 25, 2015 for Application No. 2013-537831.
US Office Action, Notice of Allowance, dated Mar. 13, 2015 for U.S. Appl. No. 13/276,725.
US Office Action, Final, dated Mar. 24, 2015 for U.S. Appl. No. 13/277,328.
US Office Action, Notice of Allowance, dated Jun. 1, 2015 for U.S. Appl. No. 13/277,328.

* cited by examiner

SURGICAL INSTRUMENT WITH MODULAR SHAFT AND TRANSDUCER

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

A variety of surgical devices employ ultrasonic energy. In some instances, ultrasonic surgical instruments may provide substantially simultaneous cutting of tissue and hemostasis by coagulation, desirably minimizing patient trauma. Examples of ultrasonic surgical instruments are disclosed in U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. Various ways in which ultrasonic surgical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

As described in greater detail below, ultrasonic surgical instruments may be constructed with modular parts such that parts can be readily replaced or otherwise changed by a user. For instance, such modularity may enable selection of different end effectors for different settings. In addition or in the alternative, replaceability may provide a dichotomy of reusable and disposable parts of a surgical instrument While a variety of ultrasonic surgical devices have been made or used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various versions of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, versions, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Device Including a Latch Configuration

Figure 1:
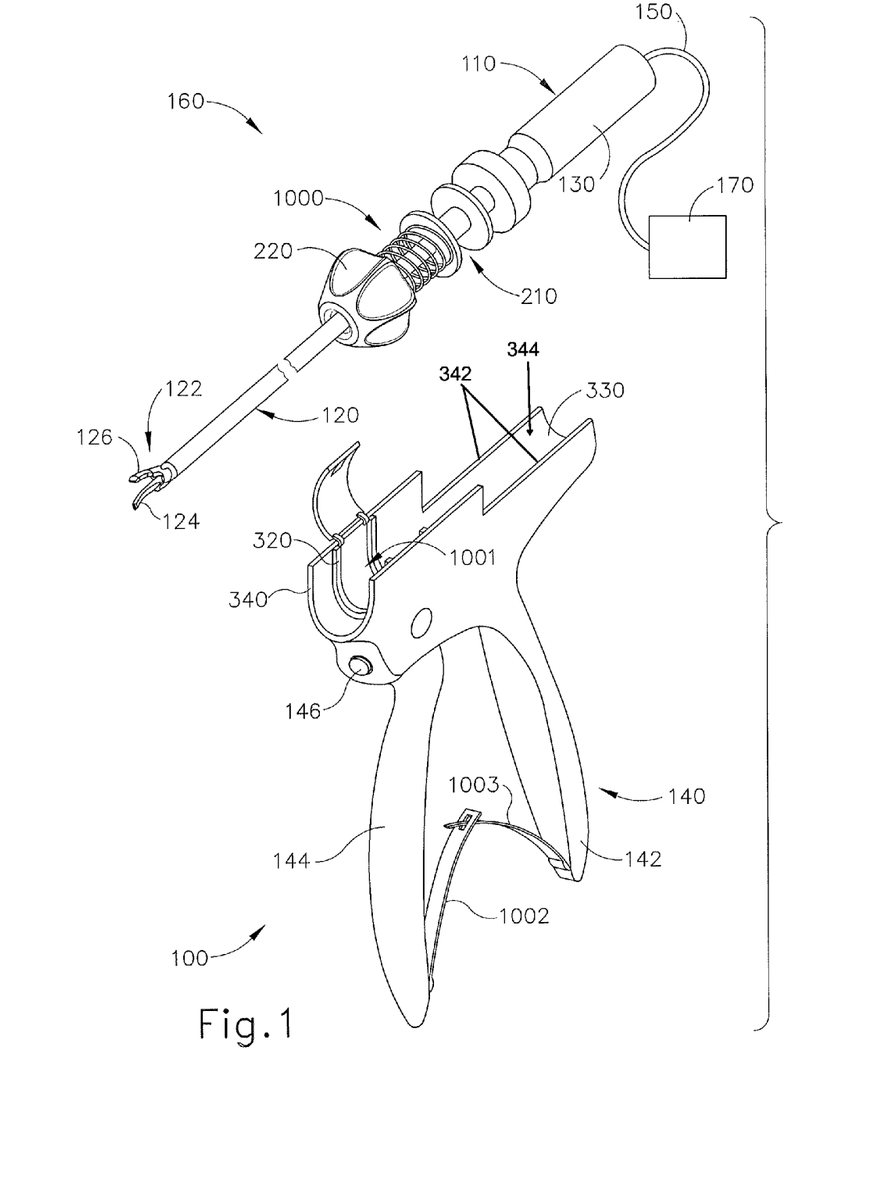
FIG. 1 depicts a partially exploded perspective view of an exemplary modular surgical device with a detachable active assembly and handle.

FIG. 1 shows an exemplary ultrasonic surgical device (100) comprising a handle (140) and a removable active assembly (160). Active assembly (160) comprises a transducer module (110) and a shaft assembly (120) that is removably coupled with transducer module (110) to form an active assembly (160). While transducer module (110) and shaft assembly (120) together may provide a user or machine with sufficient grip for manipulating and using active assembly (160), handle (140) may provide an additional grip option for the surgical device (100). Due to the modular configuration, various handle shapes and sizes may be offered to provide a user with better ergonomics and greater control of the surgical device (100). Similarly, the modular configuration may permit various types of active assemblies (160) to be used with handle (140). Transducer module (110) and handle (140) may further be provided with a locking mechanism to prevent unintended disassembly or disengagement as described in greater detail below.

In the present example, shaft assembly (120) comprises an end effector (122) disposed at a distal end of shaft assembly (120). End effector (122) comprises a harmonic blade (124) and a pivotable clamp member (126) to perform tissue cutting and sealing procedures. While harmonic blade (124) is substantially straight in the present example, it should be understood that harmonic blade (124) may alternatively be curved and/or have any other suitable configuration. It should also be understood that pivotable clamp member (126) is merely optional. By way of example only, end effector (122) may be constructed and operable in accordance with the teachings of any of the reference cited herein; and/or in any other suitable fashion. A waveguide (not shown) extends internally along the length of shaft assembly (120) and is configured to transmit ultrasonic vibrations from transducer (130) to harmonic blade (124) when shaft assembly (120) is coupled with transducer module (110). By providing active assembly (160) with a detachable shaft assembly (120), different types and/or different sizes of end effectors (122) may be installed onto transducer module (110). Additionally, by providing the detachable shaft assemblies (120), it may be possible to reduce the downtime between uses by enabling a second shaft assembly (120) to be installed on the detachable transducer module (110) while a first shaft assembly (120) is being sterilized, serviced, recycled, disposed, etc.

Transducer module (110) comprises a transducer (130) with an integral cable (150), which may further be coupled with an ultrasonic generator (170). A slip ring assembly (not shown) may be used to couple transducer (130) with cable (150), permitting transducer (130) to rotate relative to cable (150) while still maintaining electrical continuity between transducer (130) and cable (150). In the present example, generator (170) is provided externally of the surgical device (100). For instance, surgical device (100) and generator (170) may be provided and coupled in accordance with the teachings of U.S. Patent App. Publ. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should be understood, however, that a generator and/or other type of power source may be integrally provided within transducer module (110) and/or within handle (140). Merely illustrative examples of how a power source may be integrated into a surgical instrument are disclosed in one or more of the references cited herein. Transducer (130) may also be configured in accordance with teachings of any of the references cited herein; or may be otherwise configured.

Figure 2:
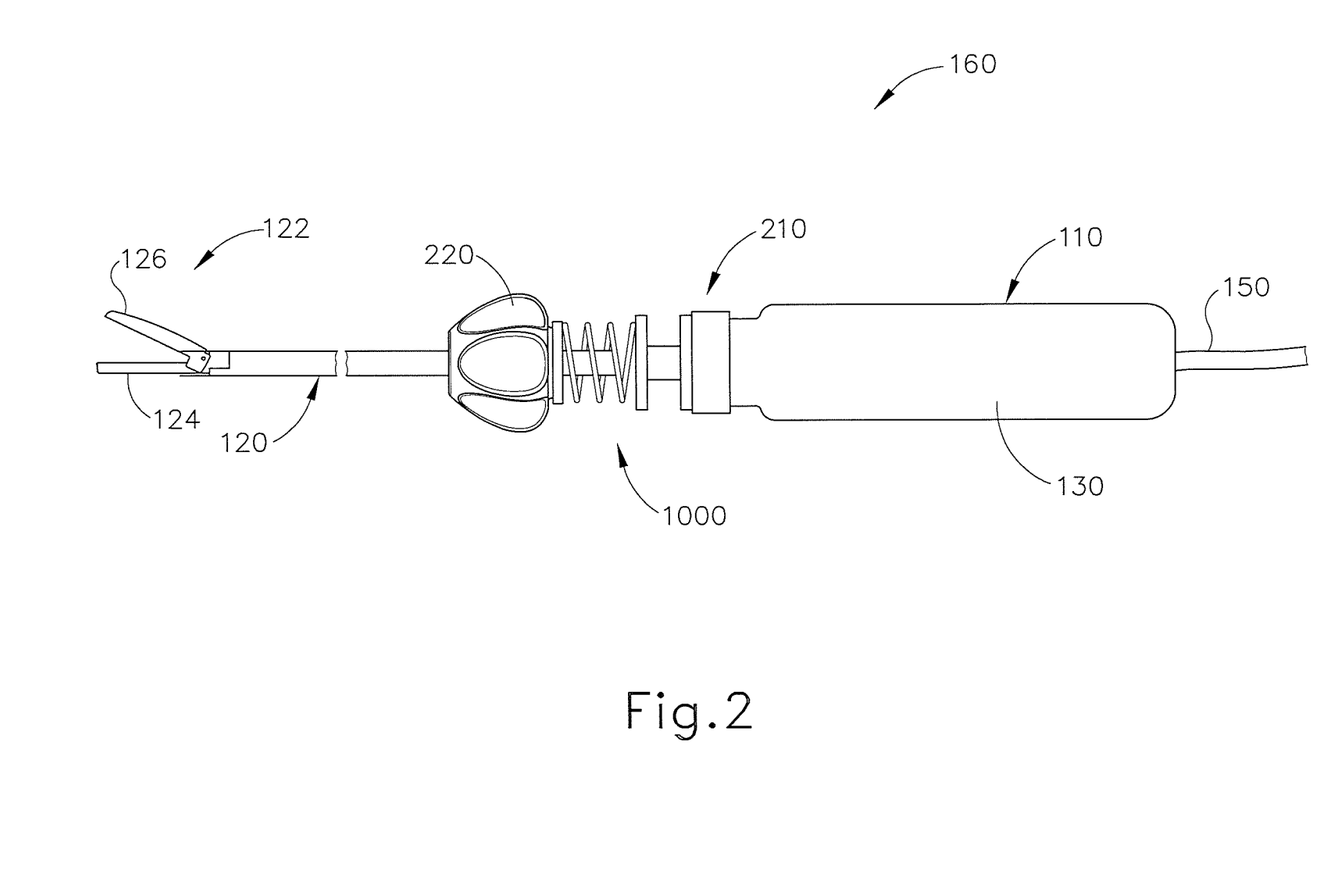
FIG. 2 depicts a side elevational view of the detachable active assembly of FIG. 1.

As noted above, active assembly (160) comprises transducer module (110) and shaft assembly (120), which may be detachably coupled with each other. Active assembly (160) further comprises features for facilitating the installation and attachment of shaft assembly (120) to transducer module (110). In particular, shaft assembly (120) of the present example comprises a grip or knob (220) located at the proximal end of shaft assembly (120). To couple shaft assembly (120) with transducer module (110), transducer module (110) and shaft assembly (120) are coaxially aligned, joined, and secured together by complementary threading. In the present example, this coupling is performed without the use of tools, by hand tightening knob (220) with one hand while holding detachable transducer module (110) with the other hand. In some versions, knob (220) includes features acting like those of a torque wrench, ensuring that the waveguide of shaft assembly (120) is coupled with transducer (130) with a sufficient amount of torque while not being over-tightened. In some other versions, a separate tool is used to help secure shaft assembly (120) to transducer module (110).

In the present example, however, active assembly (160) further comprises a clutch mechanism (210) to facilitate installation and attachment of shaft assembly (120) to transducer module (110). In some versions, clutch mechanism (210) comprises a sprag clutch to enable a user to attach and secure shaft assembly (120) to transducer module (110) without the use of a separate tool, such as a torque wrench. For instance, in some versions, knob (220) lacks any features providing functionality of a torque wrench due to such functionality being provided by clutch mechanism (210). Once clutch mechanism (210) reaches a predetermined torque, clutch mechanism (210) will prevent the transducer module (110) and shaft assembly (120) from being tightened any further. The sprag clutch may be configured to resemble a roller bearing, but instead of cylindrical rollers, non-revolving asymmetric figure-eight shaped sprags are used. In operation, when the sprag clutch rotates in one direction, the rollers slip or free-wheel, but when a torque is applied in the opposite direction, the rollers tilt slightly, producing a wedging and binding action due to friction. Of course, clutch mechanism (210) may take any other suitable form.

Handle (140) of the present example comprises a pistol grip (142), a pivoting trigger (144), and buttons (146). When active assembly (160) is coupled with handle (140), pivoting trigger (144) is operable to selectively pivot clamp member (126) toward and away from harmonic blade (124) in response to trigger (144) being squeezed toward pistol grip (142) and trigger (144) being released, respectively. Buttons (146) are operable to selectively activate transducer (130) and harmonic blade (124) in response to buttons (146) being activated. By way of example only, one button (146) may provide a relatively high level of power at harmonic blade (124) while another button (146) may provide a relatively low level of power at harmonic blade (124). As another merely illustrative example, just one activation button (146), may be provided to activate transducer (130) and harmonic blade (124) at a selected power level. Handle (140) may also include brush contacts and/or other features that provide electrical communication between buttons (146) and transducer (130) when active assembly (160) is installed in handle (140). In some versions, handle (140) and/or other components of device (100) are constructed in accordance with the teachings of U.S. Pat. No. 7,846,155, entitled "Handle Assembly Having Hand Activation for Use with an Ultrasonic Surgical Instrument," issued Dec. 7, 2010, the disclosure of which is incorporated by reference herein.

Figure 3:
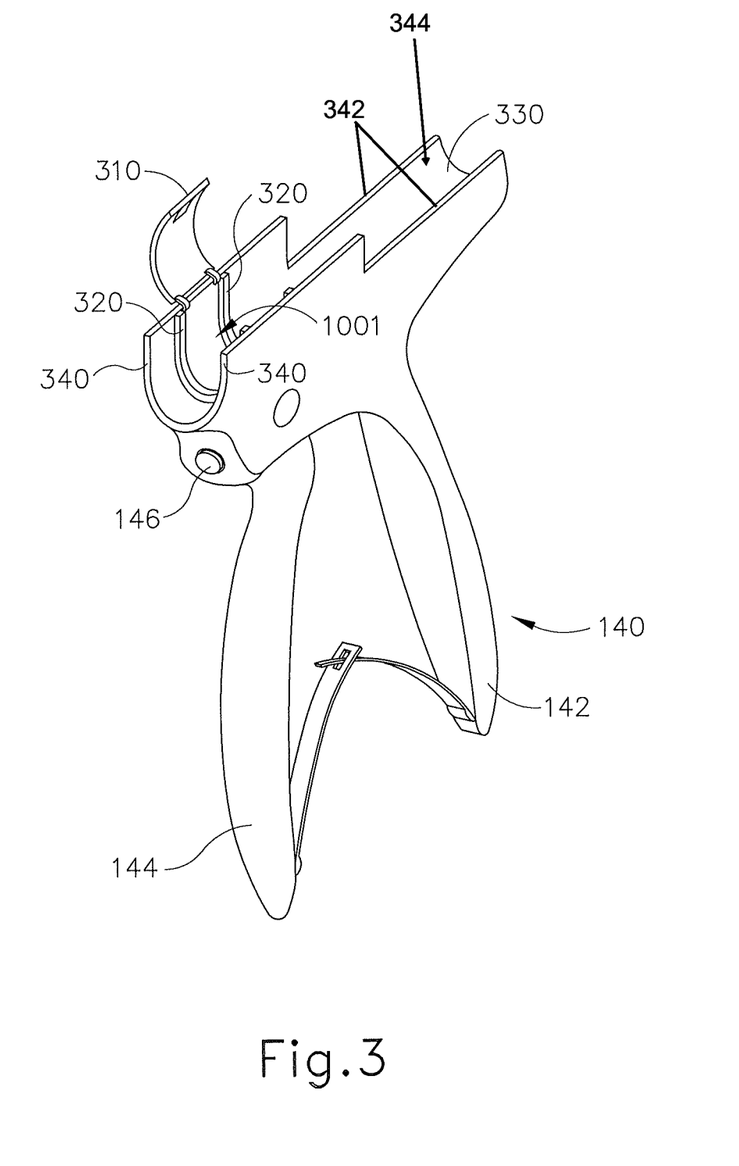
FIG. 3 depicts a perspective view of the handle of the surgical device of FIG. 1.

As best seen in FIG. 3, handle (140) of the present example is also provided with opposing wall portions (340) disposed on an upper portion of handle (140). Wall portions (340) terminate at upper edges (342), which are upwardly presented and exposed. Wall portions (340) thus define an upwardly presented open upper recess (344). Upper edges (342) extend longitudinally along the length of wall portions (340). A pivoting latch member (310) is provided on a top portion of the opposing wall portions (340) to secure active assembly (160) to handle (140). In particular, once active assembly (160) has been mounted onto handle (140), latch member (310) may be closed to secure active assembly (160) to handle (140). In the present example, latch member (310) is provided with a hinge attached to one of the upper opposing wall portions (340) and may be pivotally opened and closed. In some other versions, latch member (310) may be provided with a track or guide in order to be slid or rotated opened or closed. It should also be understood that latch member (310) may further include a cam feature (not shown) to capture and properly position active assembly (160). Handle (140) of the present example further comprises a plurality of ridges (320) to help guide active assembly (160) on to handle (140) during assembly. Such ridges (320) also restrict axial movement of active assembly (160) relative to handle (140) when latch member (310) is closed. In addition, a platform (330) is provided to align and support transducer module (110) on handle (140). Platform (330) is upwardly exposed due to separation between upper edges (342) of wall portions (340).

When active assembly (160) is placed into handle (140), trigger (144) is in a position corresponding to clamp arm (126) being open (i.e. pivoted away from harmonic blade (124)). Force limiting assembly (1000), which limits the force that can be applied to clamp arm (126) by trigger (144), is also in a position corresponding to clamp arm (126) being open. A linkage (1001) on trigger (144) is positioned such that placing active assembly (160) into handle (140) places linkage (1001) between the proximal and distal ends of force limiting assembly (1000). Force limiting assembly (1000) is operably connected to an inner actuation tube (not shown) with shaft assembly (120) that selectively pivots clamp arm (126); and movement of trigger (144) to the closed position causes corresponding movement of clamp arm (126) to the closed position through linkage (1001) and force limiting assembly (1000). Opening trigger (144) causes corresponding motion to open the clamp arm (126). Opening of the clamp arm (126) can be assisted by leaf springs (1002, 1003) situated between trigger (144) and pistol grip (142) of handle (140). Other suitable components and configurations will be apparent to those of ordinary skill in the art in view of the teachings herein.

Figure 4:
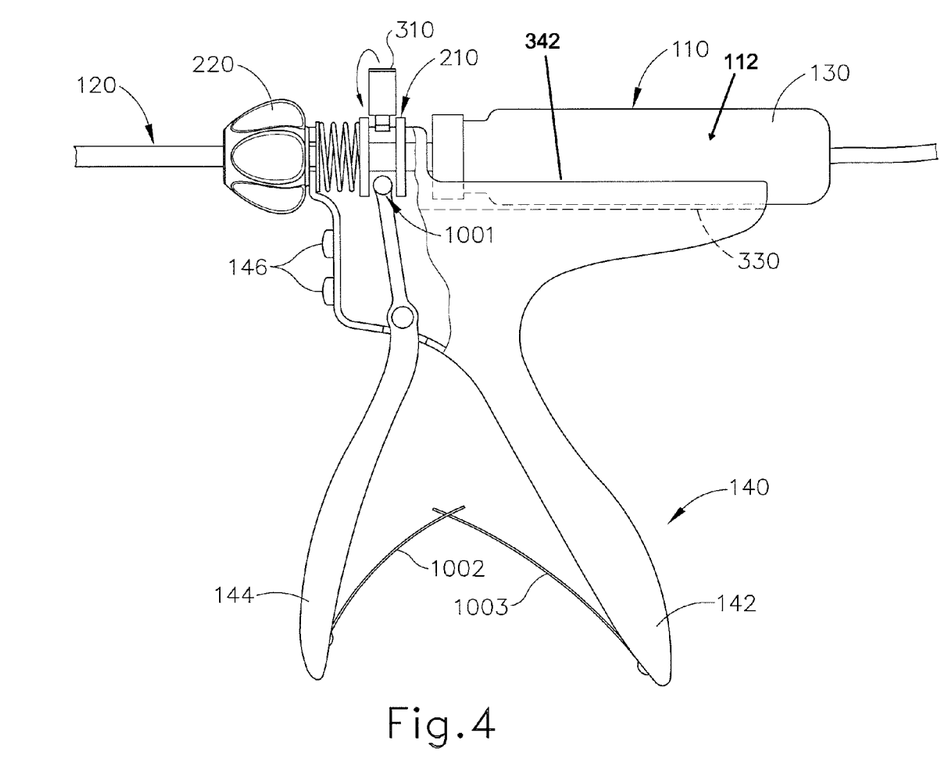
FIG. 4 depicts a side elevational view of the surgical device of FIG. 1 in an assembled configuration.
Figure 5A:
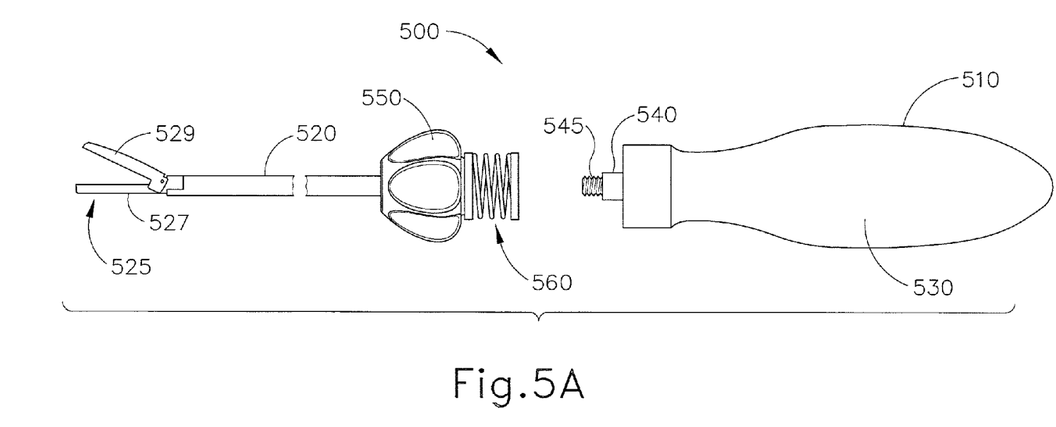
FIG. 5A depicts a side elevational view of an exemplary alternative active assembly with a shaft assembly separated from a transducer module.
Figure 5B:
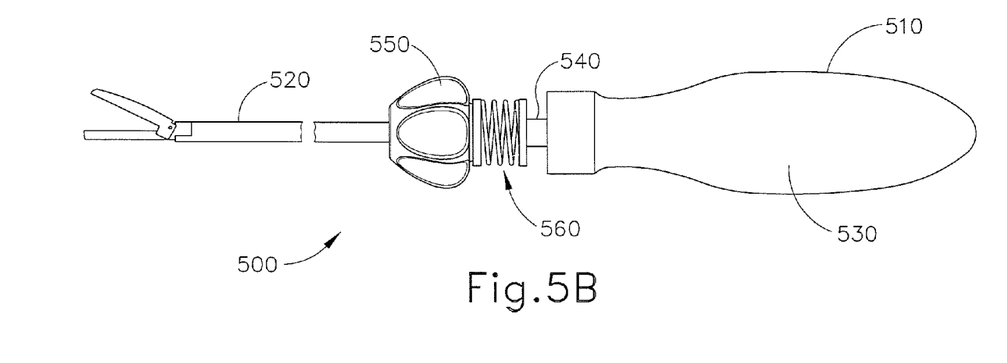
FIG. 5B depicts a side elevational view of the active assembly of FIG. 5A, with the shaft assembly coupled with the transducer module.

FIG. 4 illustrates the surgical device (100) in an intermediate assembled state. In the present example, portions between knob (220) and clutch mechanism (210) are positioned in between ridges (320) discussed above. As shown in FIG. 4, transducer module (110) is positioned above platform (330) and between upper edges (342) of wall portions (340) such that upper edges (342) extend along a portion of the length of transducer module (110). An upper portion (112) of transducer module (110) extends upwardly relative to a vertical position of upper edges (342), such that the upper portion (112) of transducer module (110) is exposed above upper edges (342). Once active assembly (160) has been mounted on handle (140), latch member (310) may be closed and may thereby serve as a clasp to secure active assembly (160) to handle (140). After the latch member (310) has been secured, the surgical device (100) will be ready for operation. In the present example, active assembly (160) may be rotatable while installed on handle (140), even with latch member (310) closed, to enable the end effector (122) to be reoriented as needed during operation. In some such versions, handle (140) and active assembly (160) may further comprise complementary stop features (not shown) that may be selectively engaged to prevent the active assembly (160) from rotating with respect to the handle (140). In some versions, such stop features may be used to prevent rotation of transducer module (110) while harmonic blade (124) and/or a waveguide that provides acoustic continuity between transducer (130) and blade (124) are/is threadably secured to transducer module (110). Such stop features may include a friction stop, ribs or pins that engage with slots or holes in the housing of transducer module (110), and/or any other suitable structures that will be apparent to those of ordinary skill in the art in view of the teachings herein. It should also be understood that a slide, button, or other feature may be provided to selectively engage/disengage such stop features II. Exemplary Surgical Device Including a Snap-Fit Configuration FIGS. 5A and 5B depict an exemplary alternative active assembly (500) comprising a detachable transducer module (510) and a shaft assembly (520), which may be detachably coupled with each other. In the present example, transducer module (510) includes transducer (530) and a waveguide (540) configured to transmit ultrasonic vibrations generated by transducer (530). Transducer (530) may be configured in accordance with teachings of any of the references cited herein; or may be otherwise configured. In the present example, waveguide (540) further comprises a first mating feature (545) for coupling with a second mating feature (not shown) of shaft assembly (520). This second mating feature is part of a waveguide (not shown) that extends internally along the length of shaft assembly (520) and is configured to transmit ultrasonic vibrations from transducer (530) to harmonic blade (527) when shaft assembly (520) is coupled with transducer module (510). The first and second mating features comprise complementary threading in the present example, though it should be understood that any other suitable configurations may be used. While end effector (525) of the present example further includes pivoting member (529) (e.g., clamp arm/pad) in addition to harmonic blade (527), it should be understood that pivoting member (529) is merely optional. It should also be understood that harmonic blade (527) may have any suitable configuration in view of the teachings herein. As discussed with the ultrasonic device (100) above, transducer module (510) may further be coupled with a generator and/or power source via a cable or otherwise.

Shaft assembly (520) of the present example comprises a grip or knob (550) disposed on the proximal end of the shaft assembly (520). End effector (525) is located at the distal end of shaft assembly (520). The modular nature of active assembly (500) enables shaft assemblies (520) with different types or different sizes of end effectors (525) to be coupled with transducer module (510). By providing the detachable shaft assembly (520), it may be possible to reduce the downtime between uses by enabling a second shaft assembly to be installed on detachable transducer module (510) while a first shaft assembly is being sterilized, serviced, recycled, disposed, etc.

During assembly, the detachable transducer module (510) and shaft assembly (520) are coaxially aligned, joined, and secured together by complementary threading. In the present example, this coupling is performed without the use of tools, by hand tightening knob (550) with one hand while holding detachable transducer module (510) with the other hand. In some versions, knob (550) includes features acting like those of a torque wrench, ensuring that the waveguide of shaft assembly (520) is coupled with transducer (530) with a sufficient amount of torque while not being over-tightened. In some other versions, a separate tool is used to help secure shaft assembly (520) to transducer module (510). Of course, the method of securing the two components may take any other suitable form. Active assembly (500) of this example further includes a spring return (560), which is configured to assist in pivoting of pivoting member (529) toward/away from blade (527). Of course, spring return (560) and/or pivoting member (529) may simply be omitted in some versions.

Figures 6, 7:
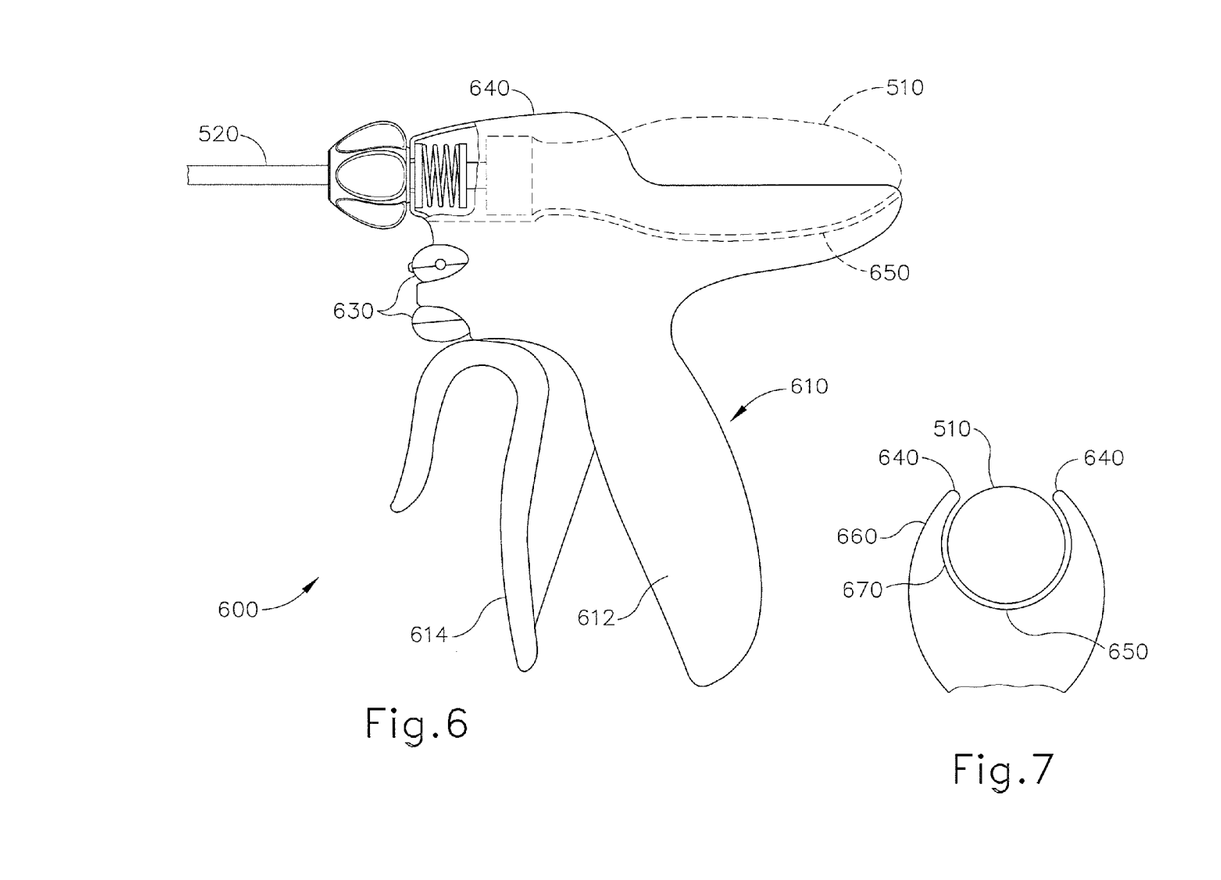
FIG. 6 depicts a side elevational view of an exemplary modular surgical device with the active assembly of FIG. 5A installed in a handle.
FIG. 7 depicts a partial view of the surgical device of FIG. 6, showing the interface of the active assembly and the handle.

FIG. 6 shows an exemplary surgical device (600) comprising active assembly (500) installed with a handle (610). While detachable transducer module (510) and shaft assembly (520) together may provide a user or machine with sufficient grip for manipulating and operating with the active assembly (500), detachable transducer module (510) and the shaft assembly (520) may further be fitted with handle (610) to provide an additional grip option for surgical device (600). Due to the modular configuration, various handle shapes and sizes may be offered to provide a user with better ergonomics and greater control of surgical device (600). Similarly, the modular configuration may permit various types of active assemblies (500) to be used with handle (610).

Handle (610) of the present example comprises a pistol grip (612), a pivoting trigger (614), and buttons (630). When active assembly (500) is coupled with handle (610), pivoting trigger (614) is operable to selectively pivot clamp member (529) toward and away from harmonic blade (527) in response to trigger (614) being squeezed toward pistol grip (612) and trigger (614) being released, respectively. Buttons (630) are operable to selectively activate transducer (510) and harmonic blade (527) in response to buttons (630) being activated. By way of example only, one button (630) may provide a relatively high level of power at harmonic blade (527) while another button (630) may provide a relatively low level of power at harmonic blade (527). As another merely illustrative example, just one activation button (630), may be provided to activate transducer (510) and harmonic blade (527) at a selected power level. Handle (610) may also include brush contacts and/or other features that provide electrical communication between buttons (630) and transducer (510) when active assembly (500) is installed in handle (610). In some versions, handle (610) and/or other components of device (600) are constructed in accordance with the teachings of U.S. Pat. No. 7,846,155, entitled "Handle Assembly Having Hand Activation for Use with an Ultrasonic Surgical Instrument," issued Dec. 7, 2010, the disclosure of which is incorporated by reference herein.

Handle (610) of the present example further comprises a platform (650), which defines part of a recess configured to receive active assembly (500). In some versions, platform (650) at least partially supports the weight of the transducer module (510). Handle (610) further includes a resilient opposing wall structure (640) disposed on an upper portion of the handle (610), adjacent to platform (650). Resilient walls (640) extend the full length of handle (610) in the present example, though it should be understood that resilient walls (640) may alternatively extend along only part of the length of handle (610). FIG. 7 shows the exemplary resilient wall structure (640) having opposing upper wall portions (660) that are configured to deflect outwardly when sufficient force is applied. In the present example, resilient wall structure (640) is narrower than a corresponding width of the detachable transducer module (510). During installation, active assembly (500) is pressed downwardly toward platform (650). The outer diameter presented by transducer module (510) exerts an outward force on upper wall portions (660) as transducer module (510) is pressed downwardly toward platform (650), causing upper wall portions (660) to deflect outwardly. Once the widest portion of transducer module (510) passes upper wall portions (660), the upper wall portions (660) resiliently deform back to their original positions, providing a snap-fit. In some versions, the upper wall portions (660) may deflect back all the way to their original positions.

Resilient wall structure (640) of the present example also includes opposing lower wall portions (670) that are approximately the same width as transducer module (510). In some versions, lower wall portions (670) may present a gap having the same or slightly narrower width than the width of detachable transducer module (510), in order to provide a snug fit. Friction between transducer module (510) and resilient wall structure (640) may substantially prevent transducer module (510) from moving or sliding longitudinally with respect to the handle (610). Such friction may also substantially prevent transducer module (510) from rotating relative to the handle (610). In some other versions, wall structure (640) may provide a clearance fit that is sufficient to retain transducer module (510) to handle (610) yet also permits transducer module (510) to rotate relative to handle (610). Other forms of assembly and other suitable relationships between the foregoing components will be apparent to those of ordinary skill in the art in view of the teachings herein.

After active assembly (500) has been secured onto handle (610), surgical device (600) will be ready for operation. In the present example, active assembly (500) may be rotatable while installed on the handle (610) to enable end effector (525) to be repositioned as needed during operation. In some versions, handle (610) and active assembly (500) may further comprise a stop member (not shown) that may be selectively engaged to prevent active assembly (500) from rotating with respect to handle (610).

III. Miscellaneous

It is contemplated that various teachings herein may be combined in numerous ways, and it should be understood that none of the teachings herein are intended to represent the limits of the inventors' contemplation. Various other examples of how several features of the surgical device (100, 600) may be carried out in practice will be apparent to those of ordinary skill in the art in view of the teachings herein, and those examples are well within the inventors' contemplation.

By way of example only, at least a portion surgical device (100, 600), active assembly (160, 500), and/or other components referred to herein may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pat. No. 7,846,155, entitled "Handle Assembly Having Hand Activation for Use with an Ultrasonic Surgical Instrument,"

issued Dec. 7, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein. Various ways in which ultrasonic surgical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery systems is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical device, comprising:
   (a) a transducer module having a proximal end and a distal end;
   (b) a shaft assembly having a proximal end and a distal end, wherein the proximal end of the shaft assembly is configured to be removably coupled with the distal end of the transducer module, wherein the transducer module is operable to transmit energy to at least part of the shaft assembly; and
   (c) a housing presenting an upwardly presented open upper recess, wherein the upwardly presented open upper recess is defined at least in part by a lower platform and a pair of opposing wall portions, wherein the opposing wall portions terminate at upwardly presented and exposed upper edges, wherein the upwardly presented open upper recess is configured to removably receive the transducer module, wherein at least one of the platform or the pair of opposing wall portions supports the transducer module, wherein an upper portion of the transducer module extends upwardly relative to a vertical position of the upper edges such that the upper portion of the transducer module is exposed above the upper edges.

2. The surgical device of claim 1, wherein the transducer module comprises an ultrasonic transducer configured to generate ultrasonic vibrations in response to electrical power.

3. The surgical device of claim 1, wherein the transducer module further comprises a cable coupled with the proximal end of the transducer module.

4. The surgical device of claim 1, wherein the transducer module further comprises a clutch mechanism located at the distal end of the transducer module.

5. The surgical device of claim 4, wherein the clutch mechanism comprises a sprag-type clutch.

6. The surgical device of claim 1, wherein the shaft assembly further comprises an end effector at the distal end of the shaft assembly, wherein the end effector includes a harmonic blade in communication with the transducer module.

7. The surgical device of claim 6, wherein the end effector further comprises a clamp member operable to pivot relative to the harmonic blade.

8. The surgical device of claim 1, wherein the shaft assembly further comprises a knob disposed at the proximal end of the shaft assembly.

9. The surgical device of claim 1, wherein the opposing wall portions are resilient, such that the opposing wall portions are configured to resiliently deflect outwardly to receive the transducer module in a snap-fit.

10. The surgical device of claim 1, wherein the opposing wall portions define a gap exposing the upper portion of the transducer module with a lower portion of the transducer module engaged by the opposing wall portions.

11. The surgical device of claim 1, wherein the housing further comprises a latch member configured to selectively retain the transducer module relative to the housing.

12. The surgical device of claim 11, wherein the latch member comprises a cam feature configured to seat one or both of the transducer module or the shaft assembly relative to the housing.

13. The surgical device of claim 11, wherein the latch member is pivotally secured to one of the opposing wall portions.

14. The surgical device of claim 1, wherein the housing comprises a handle configured to be gripped by a user's hand.

15. The surgical device of claim 14, wherein the handle comprises a pistol grip and one or more of a pivoting trigger or at least one button.

16. A surgical device, comprising:
   (a) an active assembly, the active assembly comprising:
      (i) a transducer module having a proximal end and a distal end, and
      (ii) a shaft assembly having a proximal end and a distal end, wherein the proximal end of the shaft assembly is configured to be removably coupled with the distal end of the transducer module; and
   (b) a handle having a body section, the body section comprising wall portions and a platform wherein the wall portions terminate at upper edges, wherein the upper edges are upwardly presented and exposed, wherein the wall portions define an upwardly presented open recess with the platform being upwardly exposed,
   wherein the transducer module is configured to fit in the recess, between the upper edges and above the platform.

17. The surgical device of claim 16, wherein the transducer module and shaft assembly are rotatable together relative to the handle.

18. The surgical device of claim 16, wherein the transducer module comprises an ultrasonic transducer, a cable, and a slip ring assembly coupling the ultrasonic transducer with the cable.

* * * * *